United States Patent [19]

Eckenhoff et al.

[11] Patent Number: 4,692,336

[45] Date of Patent: * Sep. 8, 1987

[54] SELF CONTROLLED RELEASE DEVICE FOR ADMINISTERING BENEFICIAL AGENT TO RECIPIENT

[75] Inventors: James B. Eckenhoff, Los Altos; Richard Cortese, Los Gatos; Felix A. Landrau, Milpitas, all of Calif.

[73] Assignee: ALZA Corporation, Palo Alto, Calif.

[ * ] Notice: The portion of the term of this patent subsequent to Jun. 17, 2003 has been disclaimed.

[21] Appl. No.: 763,365

[22] Filed: Aug. 7, 1985

Related U.S. Application Data

[63] Continuation-in-part of Ser. No. 590,778, Mar. 19, 1984, Pat. No. 4,595,583.

[51] Int. Cl.$^4$ ............................ A61K 9/22; A61M 31/00
[52] U.S. Cl. .................................... 424/468; 604/890; 604/892; 428/320.2; 424/469; 424/487
[58] Field of Search ............... 424/15, 19, 468, 469, 424/487; 604/890, 892; 428/320.2

[56] References Cited

U.S. PATENT DOCUMENTS

| | | | |
|---|---|---|---|
| 2,340,037 | 1/1944 | Zipper | 167/83 |
| 3,732,865 | 5/1973 | Higuchi et al. | 128/260 |
| 3,760,804 | 9/1973 | Higuchi et al. | 128/260 |
| 3,769,895 | 9/1973 | Higuchi | 128/260 |
| 3,845,770 | 11/1974 | Theeuwes et al. | 128/260 |
| 3,929,132 | 12/1975 | Higuchi | 128/260 |
| 3,995,632 | 12/1976 | Nakano et al. | 128/260 |
| 4,034,756 | 7/1976 | Higuchi et al. | 128/260 |
| 4,088,864 | 5/1978 | Theeuwes et al. | 219/121 |
| 4,178,361 | 12/1979 | Cohen et al. | 424/22 |
| 4,196,187 | 4/1980 | Dannelly et al. | 424/21 |
| 4,200,098 | 4/1980 | Ayer et al. | 128/260 |
| 4,235,236 | 11/1980 | Theeuwes | 128/260 |
| 4,285,987 | 8/1981 | Ayer et al. | 427/3 |
| 4,595,583 | 6/1986 | Eckenhoff et al. | 424/15 |

FOREIGN PATENT DOCUMENTS

| | | |
|---|---|---|
| 19250 | 3/1972 | Australia . |
| 2729068 | 11/1979 | Fed. Rep. of Germany . |
| 1540258 | 9/1968 | France . |

Primary Examiner—Ronald W. Griffin
Attorney, Agent, or Firm—Paul L. Sabatine; Edward L. Mandell; Steven F. Stone

[57] ABSTRACT

A dispensing device is disclosed for delivering a beneficial agent. The device comprises (1) a housing defining an internal space, (2) a heat responsive composition containing a beneficial agent in the space, (3) an expandable member in the space, and (4) at least one passageway in the housing for delivering the beneficial agent from the dispensing device.

23 Claims, 9 Drawing Figures

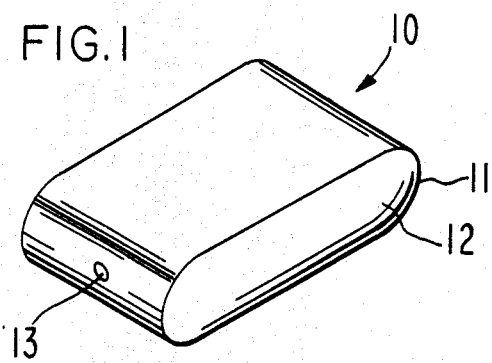
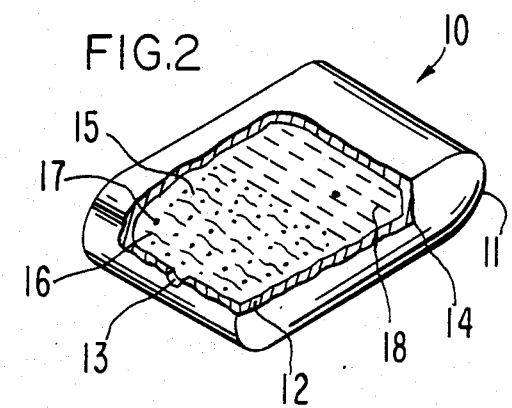
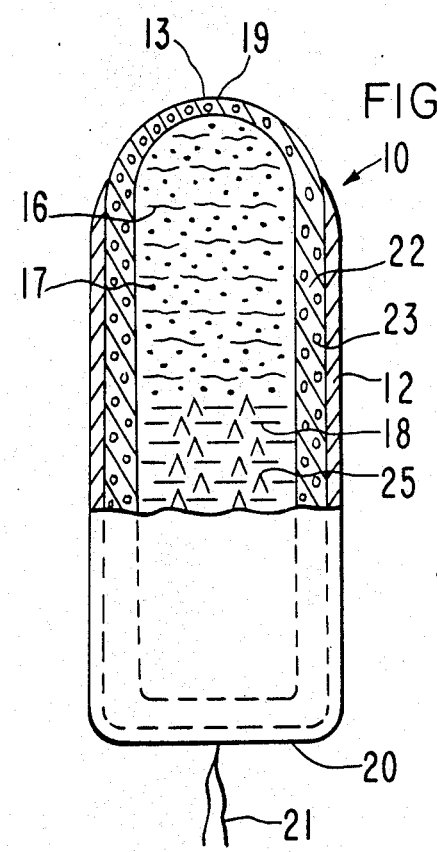
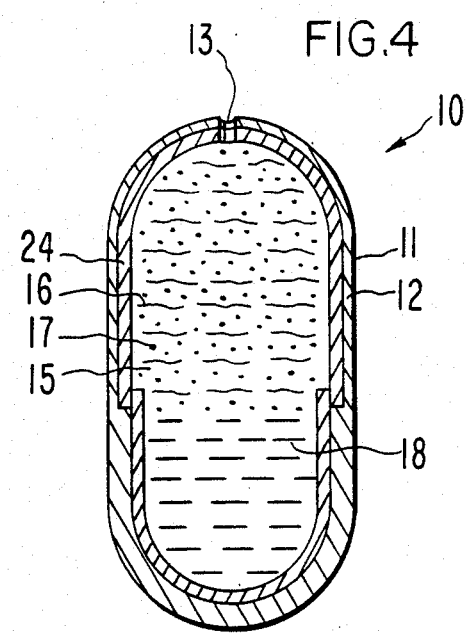
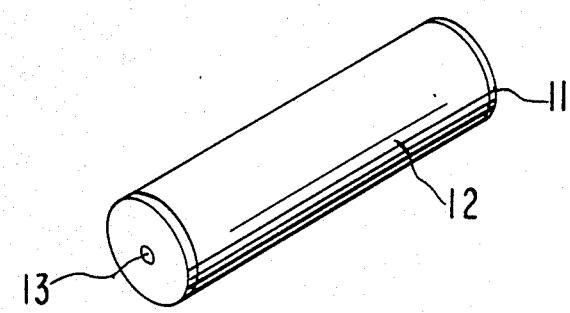

SELF CONTROLLED RELEASE DEVICE FOR ADMINISTERING BENEFICIAL AGENT TO RECIPIENT

CROSS REFERENCE TO RELATED APPLICATION

This patent application is a continuation-in-part of U.S. patent application Ser. No. 06/590,778 filed on Mar. 19, 1984 now U.S. Pat. No. 4,595,583 issued on June 17, 1986.

FIELD OF THE INVENTION

The present invention relates to a new and useful device for the controlled administration of a beneficial agent to a biological recipient. More particularly, the invention relates to a device comprising a wall that surrounds an internal lumen containing a heat-sensitive beneficial agent formulation and an expandable driving member. The invention pertains also to laminates used for manufacturing the device, to compositions useful for forming the device, and to a method for administering a beneficial agent formulation to a biological recipient.

BACKGROUND OF THE INVENTION

There has long been a need in the medical and beneficial agent dispensing arts for a device that is capable of administering a beneficial agent in a relatively controlled rate over a prolonged period of time. For example, the need exists for increasing the maximum time of therapeutic effectiveness of medicinals whose maximum time of therapeutic effectiveness, when administered in conventional dosage form such as a tablet, is only a few hours. The patient using such a conventional form must take repeated dosages at frequent intervals. Moreover, during intervals between dosages the therapeutic level in the blood decreases due to metabolic activities and the level can become so low that it is practically ineffective. Thus, as a result of frequent doses, the level of medicine available for therapy will fluctuate between doses. The need for a device exists also that can deliver beneficial agents that are difficult to deliver, usually attributable to some physical property. For example, beneficial agents that are insoluble in aqueous fluids are difficult to deliver because they do not form solutions and, accordingly, they cannot be dispensed in solution form from a dispensing device. Also, many beneficial agents exhibit lipid solubilities and these beneficial agents are difficult to deliver by conventional dosage forms.

OBJECTS OF THE INVENTION

It is a principle object of this invention to provide both a novel and useful device for dispensing a beneficial agent and which device fulfills the pressing need known to the prior art.

It is another object of this invention to provide a dispensing device that can deliver a beneficial agent at a controlled rate over a prolonged period of time thereby overcoming the shortcomings associated with the prior art dosage forms.

It is another object of this invention to provide a dispensing device that is self-contained, self-starting and self-powered in a fluid environment of use for dispensing a beneficial agent that is difficult to deliver over time.

It is another object of the invention to provide a dispensing device comprising a wall that surrounds a lumen comprising a heat sensitive means containing a beneficial agent and a driving means for delivering the beneficial agent from the dispensing device.

It is another object of this invention to provide a dispensing device comprising (1) wall-means comprising in at least a part of a wall forming composition that permits the passage of fluid and that surrounds (2) an internal lumen housing (3) a thermo-sensitive composition containing a beneficial agent and, (4) an expandable member, and which device delivers the beneficial agent by the combined physical-chemical operations of the composition melting and becoming fluid to semisolid or the like, and the expandable member swelling and occupying space in the area initially occupied by the composition, thereby dispensing the composition through means in the wall for dispensing the beneficial agent.

It is another object of this invention to provide a dispensing device that can deliver a beneficial drug contained in a thermo-responsive, lipophilic pharmaceutical acceptable carrier that softens in the presence of thermal energy absorbed from the environment of use and forms a dispensable composition and can be dispensed by the device over time.

It is another object of this invention to provide a dispensing device containing an eutetic composition comprising at least two components and at least one drug, which eutetic composition has a melting point approximately the same as the temperature of a warm-blooded animal recipient, and is dispensed from the delivery system at said temperature.

It is another object of this invention to provide a dispensing system comprising an inner positioned capsule housing a substantially aqueous-free, thermo-responsive hydrophobic composition comprising from insoluble to soluble drugs, and which thermo-responsive composition in response to energy input present in the biological environment of use, changes its form and becomes dispensable for operative delivery from the dispensing device.

It is another object of this invention to provide a dispensing device for dispensing a beneficial drug to an animal, which dispensing device contains a thermo-responsive composition and an expandable component, and which thermo-responsive composition includes a beneficial agent that is insoluble in an aqueous environment and can be housed in the dispensing device in a non-aqueous carrier that can be delivered to an animal.

It is another object of this invention to provide a laminated arrangement useful for manufacturing a dispensing device.

It is another object of the invention to provide a composition comprising a beneficial agent and a heat sensitive composition useful for manufacturing a dispensing device.

It is another object of this invention to provide a composition comprising a beneficial agent present in a nonaqueous heat sensitive composition useful for manufacturing a dispensing device.

It is another object of this invention to provide a dispensing device useful for delivering a beneficial agent to an animal.

Other objects, features and advantages of the invention will be more apparent to those skilled in the dispensing art from the following detailed description of the specification, taken in conjunction with the drawing figures and the accompanying claims.

BRIEF DESCRIPTION OF THE DRAWINGS

In the drawing figures, which are not drawn to scale, but are set forth to illustrate various embodiments of the invention, the drawing figures are as follows:

FIG. 1 is a partial view of a dispensing device designed for orally administering a beneficial agent in the gastrointestinal tract of a warm-blooded animal;

FIG. 2 is an opened view of FIG. 1 thereof for illustrating the internal structure of the dispensing device of FIG. 1;

FIG. 3 is a view of a dispensing device provided by the invention, with its wall partially broken open, which dispensing device is designed for delivering a beneficial agent into a body passageway such as the ano-rectal and vaginal passageways;

FIG. 4 is an opened view of a dispensing device for illustrating the internal structure of the dispensing system comprising an inside wall and an outside wall surrounding a lumen containing a heat sensitive composition and an expandable driving member;

FIG. 5 is a side view of a dispensing device designed and adapted for use as an implant for administering a drug at a controlled rate to an animal tissue over a prolonged period of time.

In the drawing figures and in the specification, like parts in related figures are identified by like parts. The terms appearing earlier in the specification and in the description figures, as well as embodiments thereof, are further detailed elsewhere in the disclosure.

DETAILED DESCRIPTION OF THE DRAWINGS

Figure 6:
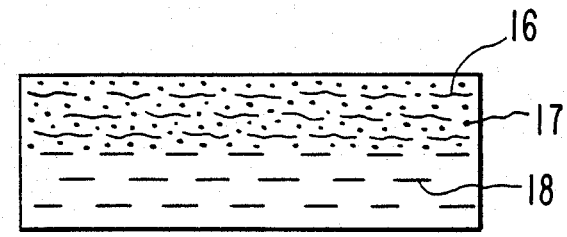
FIGS. 6, 7, 8 and 9 depict laminates useful for manufacturing the dispensing device provided by the invention.

Turning now to the drawing figures in detail, which are examples of various delivery devices provided by the invention and which examples are not to be construed as limiting, one example of a delivery device is seen in FIG. 1. In FIG. 1, delivery device 10 is seen comprising a body member 11 having a wall 12 that surrounds and forms a compartment, not seen in FIG. 1. Delivery device 10 is provided with a means 13 in wall 12 for releasing a beneficial agent from delivery device 10 to the environment of use over time.

In FIG. 2, delivery device 10 of FIG. 1 is seen in opened section, and it comprises body 11, wall 12, that surrounds and forms an internal compartment and means 13 connecting the internal compartment with the exterior of delivery device 10. Wall 12 of delivery device 10 is sectioned at 14 for depicting internal compartment 15. Wall 12 is formed of a non-toxic composition that in a presently preferred embodiment maintains its physical and chemical integrity during the delivery period, that is, it does not erode during the dispensing period. Wall 12 comprises, in one embodiment, in at least a part a wall forming composition that is substantially permeable to the passage of an external fluid. Wall 12, in another embodiment, comprises in at least a part a composition that is permeable to the passage of fluid and it is substantially impermeable to the passage of a beneficial agent and other ingredients present in delivery system 10. In another embodiment, wall 12 comprises in at least a part a permeable or a semipermeable composition with the remainder of wall 12 comprising a composition that is a means 13 for releasing a beneficial agent from delivery system 10.

Internal compartment 15 contains a heat sensitive, thermo-responsive composition 16, identified by wavy lines, homogeneously or heterogeneously containing a beneficial agent formulation 17, represented by dots. Internal compartment 15 further contains an expandable driving member 18, identified by dashes, that is in layered contact with a contacting surface formed by the interface of thermo-responsive composition 16 and expandable member 18. Both thermo-responsive composition 16 and expandable member 18 have a shape that corresponds to the internal shape of compartment 15. Means 13 extends through wall 12 for connecting compartment 15 with the exterior of delivery device 10. In FIGS. 1 and 2, means 13, in one embodiment, is a passageway for delivering beneficial agent formulation 17 from delivery device 10 to the environment of use.

FIG. 3 depicts another embodiment of delivery device 10 provided by the invention. FIG. 3 depicts delivery device 10 designed for easy placement in a body passageway, such as a vagina or the ano-rectal passageways. Delivery device 10 has an elongated, cylindrical, self-sustaining shape, and it comprises a rounded lead end 19 and a trailing end 20 suitably equipped with a manually controlled string 21 for easily delivering device 10 from a body passageway. FIG. 3 is an opened view of delivery device 10. In FIG. 3, delivery device 10 comprises an internal wall 22 formed in at least a part of a microporous composition. Wall 22 in one embodiment contains a pore forming agent that is removed from wall 22 in the environment of use to form pores of controlled dimensions 23, or in another embodiment wall 22 comprises a microporous composition consisting of a plurality of micropores of controlled dimensions. In either embodiment of wall 22, lead end 19 is a means for dispensing a beneficial agent from delivery device 10. Device 10 further comprises an exterior wall 12 laminated in at least a part to interior wall 22. Exterior wall 12 is formed in at least a part of a permeable composition or in at least a part of a semipermeable composition permeable to the passage of fluid and, in the latter embodiment, substantially impermeable to the passage of beneficial agent. The laminated wall surrounds an internal compartment 15 containing thermoresponsive heat composition 16 containing beneficial agent 17. Thermo-responsive heat composition 16 is immediately adjacent to the interior surface of microporous wall 22 for passage through micropores 23. Compartment 15 contains also an expandable driving member 18 in laminar arrangement with thermo-responsive composition 16. Device 10 in a preferred embodiment contains a beneficial therapeutic agent, that is a drug, designed for absorption by the vaginal mucosa, or by the ano-rectal mucosa, to produce a local or a systemic effect. The microporous drug releasing surface is an added advantage that acts like a diffuser for diffusing the drug over a larger receiving surface, thereby presenting the drug over a broad tissue area for lessening the incidence of tissue irritation.

FIG. 4 illustrates another embodiment of a delivery device 10 provided by the invention. FIG. 4 is an opened view of the therapeutic delivery device. Delivery device 10 of FIG. 4 comprises body 11, external wall 12 and a passageway 13. Wall 12 surrounds an internal capsule wall 14 and internal compartment 15. Wall 12, in one embodiment comprises a fluid permeable wall-forming composition, or wall 12 in another embodiment comprises a semipermeable wall-forming composition that is permeable to the passage of an external fluid present in the environment of use, and it is substantially impermeable to the passage of a beneficial agent and other ingredients contained in compartment 15. In another embodiment a semipermeable wall 12 can partly surround internal capsule 24 and the rest of wall 12 can comprise a different composition. Compartment 15 contains a thermo-responsive, heat sensitive composition 16 containing beneficial agent 17, and an expandable driving member 18 that is in layered contact with a contacting surface of thermo-responsive composition 16. A passageway 13 extends through outer semipermeable wall 12 and internal capsule wall 24 for completing communication between compartment 15 and the exterior of delivery device 10.

FIG. 5 depicts a pharmaceutical delivery device particularly adapted for use as a depot implant. Delivery device implant 10 is manufactured for administering a drug to an animal. Delivery device 10 implant comprises a body 11, wall 12 and releasing means 13. Delivery device 10 implant is structurally identical with device 10 as described above and it operates in a like manner. Delivery device 10 implant is used by placing the implant within the animal body, such as in a muscle tissue, where it administers drug at a controlled and continuous rate over a prolonged period of time. One advantageous use of the present implant is in surgical operations accompanied by severe pain after the operation is completed and the patient regains consciousness. In these cases, the implant containing an analgesic can be topically or subcutaneously implanted into a muscle during the operation. The implant releases the analgesic and eases pain throughout the recovery period, and then it is easily removed from the muscle.

Delivery device 10 of FIGS. 1 through 5, when in operation, delivers beneficial agent formulation 17 to an animal fluid environment of use by a combination of thermodynamic and kinetic integrally performed activities. That is, in operation, heat sensitive lipophilic, hydrophilic composition 16 in response to the temperature of an animal recipient absorbs thermal energy, softens and/or melts and forms a fluidic or a semipaste like deliverable composition for delivering beneficial agent 17 through means 13. As composition 16 absorbs thermal energy and undergoes change, concomitantly external fluid is imbibed through a semipermeable wall 12 by expandable hydrophilic layer 18 in a tendency towards osmotic equilibrium, to continuously expand and swell layer 18. Layer 18 expands, in an embodiment, while establishing and maintaining an intact immiscible boundary defined by heat-sensitive, aqueous-free composition 16 and expandable aqueous-containing layer 18. The expansion and swelling of layer 18 causes it to increase in volume thereby urging it to push against heat sensitive composition 16. As expanding layer 18 occupies space in compartment 15 it urges composition 16 containing agent 17 through means 13. Further in operation, as seen in FIG. 4, as fluid is imbibed into device 10 through wall 12 the inner thin-walled watered soluble capsule member 24 dissolves at a body temperature of 37° C. or more, leaving device 10 with semipermeable wall 12. The dissolved gelatin blends can blend with composition 16 and it can also lubricate the inside surface of wall 12.

While FIGS. 1 through 5 are illustrative of various devices 10 that can be made according to the invention, it is to be understood these devices are not to be construed as limited, as device 10 can take a wide variety of shapes, sizes and forms for delivering agent 17 to the environment of use. For example delivery device 10 can be designed for oral use for releasing a locally or systemically acting therapeutic agent in the gastrointestinal tract over time. Oral device 10 can have various conventional shapes and sizes such as round with a diameter of ⅛ inch to 9/16 inches, or it can be shaped like a capsule having a range of sizes from triple zero to zero and from 1 to 8. Also, delivery device 10 can be adapted, shaped, sized and structured as a buccal, cervical, intrauterine, nasal, dermal, subcutaneous, and artificial gland device. The device can be used for administering a beneficial agent to animals, including warm-blooded mammals, humans, avians, reptiles and fishes. The delivery device can be used in hospitals, clinics, nursing homes, farms, zoos, veterinary clinics, sickrooms, and other environments of use.

DETAILED DESCRIPTION OF THE INVENTION

In accordance with the practice of this invention, it has now been found that wall 12 can be manufactured of a wall forming composition that does not adversely affect agent 17, an animal, or other host, and it is permeable in at least a part to the passage of an external aqueous type fluid, such as water and biological fluid. In these embodiments, wall 12 can be formed of semipermeable or permeable materials. Typical materials for forming wall 12 in whole or in part, include semipermeable polymers known to the art as osmosis and reverse osmosis membranes, that are permeable to the passage of fluid while remaining essentially impermeable to the passage of agents, including drugs and the like. These materials comprise semipermeable homopolymers, semipermeable copolymers, and the like. In one embodiment typical materials include cellulose esters, cellulose monoesters, cellulose diesters, cellulose triesters, cellulose ethers, and cellulose ester-ethers, mixtures thereof, and the like. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkoxy, halogen, carboalkyl, alkylcarbamate, alkylcarbonate, alkylsulfonate, alkylsulfamate, and like semipermeable polymer forming groups.

The semipermeable materials typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di- and tri-alkenylates, mono-, di- and tri-aroylates, and the like. Exemplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S. of 2 to 3 and an acetyl content of 34 to 44.8%, and the like. More specific cellulosic polymers include cellulose propionate having a D.S. of 1.8 and a propionyl content of 38.5%; cellulose acetate propionate having an acetyl content of 1.5 to 7% and a propionyl content of 39 to 42%; cellulose acetate propionate having an acetyl content of 2.5 to 3%, an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%, cellulose acetate butyrate having an acetyl content of 2 to 29.5%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate; cellulose propionate morpholinobutyrate; cellulose acetate butyrate; cellulose acetate phthalate, and the like; mixed cellulose esters such as cellulose acetate valerate; cellulose acetate succinate; cellulose propionate succinate; cellulose acetate octanoate; cellulose valerate palmitate; cellulose acetate heptonate, and the like. Semipermeable polymers are known in U.S. Pat. No. 4,077,407 and they can be made by procedures described in *Encyclopedia of Polymer Science and Technology*, Vol. 3, pp 325–354, 1964, published by Interscience Publishers, Inc., New York.

Additional semipermeable polymers include acetaldehyde dimethyl cellulose acetate; cellulose acetate ethylcarbamate; cellulose acetate methylcarbamate; cellulose dimethylaminoacetate; a cellulose composition comprising cellulose acetate and hydroxypropyl methylcellulose; a composition comprising cellulose acetate and cellulose acetate butyrate; a cellulose composition comprising cellulose acetate butyrate and hydroxypropyl methylcellulose; semipermeable polyamides; semipermeable polyurethanes; semipermeable polysulfanes; semipermeable sulfonated polystyrenes, cross-linked, selectively semipermeable polymers formed by the coprecipitation of a polyanion and a polycation as disclosed in U.S. Pat. Nos. 3,173,876; 3,276,586; 3,541,005; 3,541,006, and 3,546,142; selectively semipermeable silicon rubbers; semipermeable polymers as disclosed by Loeb and Sourirajan in U.S. Pat. No. 3,133,132; semipermeable polystyrene derivatives; semipermeable (polysodiumstyrenesulfonate); semipermeable polymer exhibiting a fluid permeability of $10^{-1}$ to $10^{-7}$ (cc.mil/cm$^2$hr.atm) expressed as per atmosphere of hydrostatic or osmotic pressure difference across a semipermeable wall. The polymers are known in the art in U.S. Pat. Nos. 3,845,770; 3,916,899 and 4,160,020, and in *Handbook of Common Polymers*, by Scott, J. R. and Roff, W. J., 1971, published by CRC Press, Cleveland, Ohio.

Other noncellulosic materials for forming wall 12 include polyolefins, vinyl-type polymers, condensation-type polymers, and rubber-type polymers. The materials permit the passage of fluid, and they substantially maintain the presence of expandable member 18 in compartment 15 during operation of device 10. Exemplary materials include polyethylene, polypropylene, ethylene-vinyl acetate copolymer, polybutene, polyvinyl acetate, cross-linked polyvinyl alcohol, plasticized polyamides, polyesters, polycarbonates, polyisoprene, polybutadiene, polyvinyl butyryl, and the like.

The microporous materials used for forming wall 19 generally can be described as having a sponge-like appearance that provides a supporting structure for interconnected pores or voids. The material can be isotropic wherein the structure is homogeneous throughout a cross-sectional area, the material can be anisotropic wherein the structure is non-homogeneous throughout a cross-sectional area, or the materials can have both cross-sectional areas. The materials are opened-celled, as the pores are continuous or connected pores having an opening on both faces of microporous wall 19. The micropores are interconnected through tortuous paths of regular and irregular shapes including curved, linear, curved-linear, randomly oriented continuous pores, hindered connected pores and other interconnected porous paths discernible by microscopic examination.

Generally the microporous walls are characterized as having a reduced bulk density as compared to the bulk density of the corresponding non-porous precursor microporous wall. The morphological structure of the total microporous wall will have a greater proportion of total surface area than the non-porous wall. The microporous wall can be further characterized by the pore size, the number of pores, the tortuosity of the microporous paths, and the porosity which relates to the size and the number of pores. The pore size of a microporous wall is easily ascertained by measuring the observed pore diameter at the surface of the material under the electron microscope. Generally materials possessing from 5% to 95% pores, and having a pores size of from 10 angstroms to 100 microns can be used for making wall 19. Relationships of the above type are discussed in *Transport Phenomena In Membranes*, by Lakshminatayamah, N., Chapter 6, 1969, published by Academic Press, Inc., New York. Microporous materials are described in *Science*, Vol. 170, pp 1302–1305, 1970; *Nature*, Vol. 214, p 285, 1967; *Polymer Engineering and Science*, Vol. 11, pp 284–388, 1971; U.S. Pat. Nos. 3,567,809 and 3,751,537; and in *Industrial Processing With Membranes* by Lacey, R. E. and Loeb, Sidney, pp 131–134, 1972, published by Wiley Interscience, New York.

Microporous materials are commercially available and they can be made by art-known methods. The materials can be made by etched nuclear tracking; by cooling a solution of a flowable polymer below the freezing point whereby the solvent evaporates from the solution in the form of crystals dispersed in the polymer, and then curing the polymer followed by removing the solvent crystals; by cold stretching or hot stretching at low or high temperatures until pores are formed; by leaching from a polymer a soluble component by an appropriate solvent; by ion exchange reaction; and by polyelectrolyte processes. In a presently preferred embodiment, the microporous wall is formed in the environment of use from a precursor microporous wall. This latter wall contains a poreformer that is removed from the precursor by dissolving or leaching a pore former therefrom, thus forming an operable microporous wall. The pore-formers useful for the present purpose are a member selected from the group consisting of about 1 to 50%, or more by weight of a solid pore-former, about 0.5 to 20% percent by weight of a liquid pore-former, and mixtures thereof. In another embodiment, the microporous wall can be formed by a compression coating technique. In this latter embodiment, a rigid microporous wall substantially free of substances soluble or swellable in the fluid present in the environment of use can be formed by compression coating a microporous material around the compartment forming ingredients. Generally a microporous wall is formed under a compression pressure of 500 to 5000 kg/cm$^2$, usually in a rotary machine. Processes for preparing microporous walls are described in *Synthetic Polymer Membranes*, by R. E. Kesting, Chapt. 4 & 5, 1971, published by McGraw-Hill, Inc.; *Chemical Reviews*, Vol. 18, p 373–455, 1934; *Polymer Engineering and Science*, Vol. 11, p 284–288, 1971; *J. Appln. Poly. Sci.*, Vol. 15, pp 811-829, 1971; in U.S. Pat. Nos. 3,565,259; 3,615,024; 3,751,536; 3,801,692; 3,852,224; 3,849,528 and 3,929,509, and in British Patent No. 1,459,356.

Materials suitable for forming a microporous wall include polycarbonates comprising linear polyesters of carbonic acid in which carbonate groups recur in polymer chains by phosgenation of a dihydroxy aromatic such as a bisphenol, microporous poly(vinyl chloride), microporous polyamides such as polyhexamethylene adipamide, microporous modacrylic copolymers including those formed of polyvinylchloride and acrylonitrite, styrene-acrylic acid copolymers, microporous polysulfones characterized by diphenylene sulfone groups in the linear chain thereof, halogenated polymers such as polyvinylidene fluoride, polyvinylfluoride and polyfluorohalocarbon, polychloroethers, cellulose esters, cellulose ethers, cellulose acylates, acetal polymers such as polyformaldehyde, polyesters prepared by esterification of a dicarboxylic acid or anhydride with a polyol, poly(alkylenesulfides), phenolic polyesters, microporous poly(saccharides) having substituted and unsubstituted anhydroglucose units, asymmetric porous polymers, cross-linked olefin polymers, hydrophobic and hydrophilic microporous homopolymers, copolymers or interpolymers having a reduced bulk density, and the materials described in U.S. Pat. Nos. 3,595,752; 3,643,178; 3,654,066; 3,709774; 3,718,532; 3,803,061; 3,852,224; 3,852,388; 3,853,631 and 3,948,254; in British Patent No. 1,126,849; in Chem. Absts., Vol. 71, 4274F, 22572F; and 22573F, 1969.

Additional microporous materials include materials that are substantially insoluble in the fluid present in the environment of use, are inert, non-disintegrating, noneroding and are materials that can be compressed in powder form, applied by air suspension, dipping techniques, and the like. Exemplary materials include poly(urethanes), copolymers of divinyl chloride and acrylonitrile, organic materials such as crosslinked chain-extended poly(urethanes), microporous poly(urethanes) in U.S. Pat. No. 3,524,753; poly(imides), poly(benzimidazoles), collodion (cellulose nitrate with 11% nitrogen), regenerated proteins, microporous materials prepared by diffusion of a multivalent cations into polyelectrolyte sols in U.S. Pat. No. 3,565,259, anisotropic microporous materials of ionically associated polyelectrolytes, microporous polymers formed by the coprecipitation of a polycation and a polyanion as described in U.S. Pat. Nos. 3,276,589; 3,541,006; and 3,546,142, derivatives of poly(styrene) such as poly(sodium styrene sulfone) and poly(vinylbenzyltrimethyl-ammonium chloride), the microporous materials discussed in U.S. Pat. Nos. 3,615,024; 3,646,178; and 3,852,224, the microporous walls having a plurality of micropores as disclosed in U.S. Pat. No. 3,948,254; and the like.

The expression "pore-former", includes pore-forming solids and pore-forming liquids. In the later expression, the term, "liquid" generically embraces semi-solids, pastes and viscous fluids. The poreformers can be inorganic or organic. The term, "pore-former" for both solids and liquids include substances that can be dissolved, extracted or leeched from the precursor microporous wall by fluid present in the environment of use to form an operable, open-celled type microporous wall. Additionally, the pore-formers suitable for the invention include poreformers that can be dissolved, leached, or extracted without causing physical or chemical changes in the polymer. The pore-forming solids can have a size of about 0.1 to 200 microns and they include alkali metals salts such as lithium chloride, lithium carbonate, sodium chloride, sodium bromide, sodium carbonate, potassium chloride, potassium sulfate, potassium phosphate, sodium benzoate, sodium acetate, sodium citrate, potassium nitrate, and the like. The alkaline earth metal salts such as calcium phosphate, calcium nitrate, calcium chloride, and the like. The transition metal salts such as ferric chloride, ferrous sulfate, zinc sulfate, cupric chloride, manganese fluoride, manganese fluorosilicate, and the like. Organic compounds such as polysaccharides including sucrose, glucose, fructose, mannitol, mannose, galactose, aldohexose, altrose, talose, sorbitol, and the like. Organic aliphatic and aromatic ols including diols, polyols; organic ols including diols and polyols, and other polyols such as polyhydric alcohol, polyalkylene glycol, polyglycol, poly ($\alpha$-$\omega$)-alkylenediols, and the like. The pore-formers are nontoxic and on their removal from the wall channels are formed through the wall that fills with fluid. The channels become, in one embodiment, means or paths for releasing a beneficial agent from the delivery device. The pores extend from the inside wall to the outside wall for effective release of beneficial agent to the exterior of the delivery system. In a presently preferred embodiment, the wall comprises 1 to 50% of pore-former based on the weight of the polymer of a pore-forming agent selected from the group consisting of inorganic salts, organic salts, carbohydrates, and ols that are used when the pores of controlled porosity are formed during use in a biological environment.

Expandable member 18 housed in compartment 15 generally comprises a hydrogel composition. The hydrogel composition is noncross-linked or it is optionally cross-linked, and it can possesses properties, such as the ability to absorb or imbibe an exterior fluid through a semipermeable wall 12. When the hydrogel possesses osmotic properties it exhibits an osmotic pressure gradient across a semipermeable wall 12 against a fluid outside delivery system 10. The materials used for forming the swellable, expandable hydrogel are polymeric materials neat, and polymeric materials blended with osmotic agents that interact with water or a biological fluid, absorb the fluid and swell or expand to an equilibrium states. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also known as osmopolymers can be noncross-linked or lightly cross-linked. The cross-links can be covalent or ionic bonds with the polymer possessing the ability to swell in the presence of fluid, and when cross-linked it will not dissolve in the fluid. The polymer can be of plant, animal or synthetic origin. Polymeric materials useful for the present purpose include poly(hydroxyalkyl methacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(vinyl alcohol) having a low acetate residual; a swellable mixture of agar and carboxymethyl cellulose; a swellable composition comprising methyl cellulose mixed with a sparingly cross-linked agar; a water-swellable copolymer produced by a dispersion of finely divided copolymer of maleic anhydride with styrene, ethylene, propylene, or isobutylene; water swellable polymer of N-vinyl lactams; and the like.

Other gelable, fluid absorbing and/or imbibing and retaining polymers useful for forming the hydrophilic, expandable push member include pectin having a molecular weight ranging from 30,000 to 300,000; polysaccharides such as agar, acacia, karaya, tragacanth, algins and aguar; Carbopol ® acidic carboxy polymer and it salt derivatives; polyacrylamides; water-swellable indene maleic anhydride polymers; Goodrite ®polyacrylic acid having a molecular weight of 80,000 to 200,000; Polyox ® polyethylene oxide polymers having a molecular weight of 100,000 to 5,000,000; starch graft copolymers; Aqua-Keep ® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000, and the like. In a preferred embodiment, the expandable member comprises polymers and polymeric compositions that are thermoformable. Representative polymers possessing hydrophilic properties are known in U.S. Pat. Nos. 3,865,108; 4,002,173; 4,327,725, and in *Handbook of Common Polymers*, by Scott and Roff, published by Cleveland Rubber Company, Cleveland, Ohio.

The swellable, expandable polymer, in addition to providing a driving source for delivering a beneficial agent from the dispenser 10, further serves to function as a supporting matrix for an osmotically effective solute. The osmotic solute can be homogeneously or heterogeneously blended with the polymer to yield the desired expandable member 18. The composition in a presently preferred embodiment comprises at least one polymer and at least one osmotic solute. Generally a composition will comprise about 20% to 90% by weight of polymer and 80% to 10% by weight of osmotic solute, with a presently preferred composition comprising 35% to 75% by weight of polymer and 65% to 25% by weight of osmotic solute.

The osmotically effective compound that can be blended homogeneously or heterogeneously with the swellable polymer, to form a push or driving member, are the osmotically effective solutes that are soluble in fluid imbibed into the swellable polymer, and exhibit an osmotic pressure gradient across a semipermeable wall against an exterior fluid. Osmotically effective compounds and solutes are known also as osmagents. Osmotically effective osmagents useful for the present purpose include magnesium sulfate, magnesium chloride, sodium chloride, lithium chloride, potassium chloride, potassium sulfate, sodium sulfate, mannitol, urea, sorbitol, inositol, succrose, glucose, and the like. The osmotic pressure in atmospheres, ATM, of the osmagents suitable for the invention will be greater than zero ATM, generally from eight ATM up to 500 ATM, or higher.

The thermo-responsive composition 16, containing beneficial agent 17 homogeneously or heterogeneously dispersed or dissolved therein, is formed in a presently preferred embodiment a heat sensitive, hydrophobic material that exhibits solid-like properties at room temperature up to 25° C., and within a few centigrade degrees thereof, and exhibits in a melting point or a softening point over a range of 25° C. to 45° C. In a preferred embodiment the degrees approximate mammalian body temperatures of 37° C., and with a few centigrade degrees thereof. The present invention uses the phrases, "melting point", "softening point", "pour point", or "liquifies", to indicate the temperature at which the thermo-responsive composition melts, undergoes dissolution, forms a paste-like ribbon, or dissolves to form a dispensable carrier so it can be used for beneficial agent 17 from a dispenser 10.

The term "thermo-responsive" as used for the purpose of this invention includes thermoplastic compositions comprising means capable of become dispensable in response to heat and solidifying or thickening again when cooled. The term also includes thermotropic compositions capable of undergoing change in response to the application of thermal energy in a gradient manner, and they are temperature sensitive in their response to the application or withdrawl of energy. The term, "thermo-responsive" as used for the purpose of this invention in a preferred embodiment denotes the physical-chemical property of a composition agent carrier to exhibit solid, or solid-like properties at temperatures up to 25° C, and become fluid, semisolid, or viscous when contacted by heat at temperatures from 31° C., usually in the range of 25° C. to 45° C. The thermo-responsive carrier is heat-sensitive and preferably anhydrous and it has the property of melting, dissolving, undergoing dissolution, softening, or liquifying at the elevated temperatures, thereby making it possible for the dispenser 10 to deliver the thermo-responsive carrier with the beneficial agent 17 homogeneously or heterogeneously blended therein. The thermo-responsive carrier is preferably lipophilic and hydrophobic. Another important property of the carrier is its ability to maintain the stability of the agent contained therein during storage and during delivery of the agent. Representative thermo-responsive compositions and their melting points are as follows: cocoa butter, 32°-34° C.; cocoa butter plus 2% beeswax, 35°-37° C.; propylene glycol monostearate and distearate, 32°-35° C.; hydrogenated oils such as hydrogenated vegetable oil, 36°-37.5° C.; 80% hydrogenated vegetable oil and 20% sorbitan monopalmitate, 39°-39.5° C.; 80% hydrogenated vegetable oil and 20% poly-sorbate 60, 36°-37° C.; 77.5% hydrogenated vegetable oil, 20% sorbitan trioleate and 2.5% beeswax, 35°-36° C.; 72.5% hydrogenated vegetable oil, 20% sorbitan trioleate, 2.5% beeswax and 5.0% distilled water, 37°-38° C., mono-, di-, and triglycerides of acids having from 8-22 carbon atoms including saturated and unsaturated acids such as palmitic, stearic, oleic, lineolic, linolenic and archidonic; glycerides of fatty acids having a melting point of at least 32° C., such as monoglycerides, diglycerides and triglycerides of vegetable fatty acids having 10 to 18 atoms obtained from coconut oil, olive oil and the like; partially hydrogenated cottonseed oil, olive oil and the like; partially hydrogenated cottonseed oil, 35°-39° C; hardened fatty alcohols and fats, 33°-36° C.; hexadienol and hydrous lanolin triethanolamine glyceryl mono-stearate, 38° C., eutetic mixtures of mono-, di-, and triglycerides, 35°-39° C.; Witepsol®H15, triglyceride of saturated vegetable fatty acid with monoglycerides, 33.5°-35.5° C.; Witepsol ®H32 free of hydroxyl groups, 31°-33° C.; Witepsol ®W25 having a saponification value of 225-240 and a melting point of 33.5°-35.5° C.; Witepsol-®E75 having a saponification value of 220-230 and a melting point of 37°-39° C.; a polyalkylene glycol such as polyethylene glycol 1000, a linear polymer of ethylene oxide, 38°-41° C.; polyethylene glycol 1500, melting at 38°-41° C.; polyethylene glycol monostearate, 39°-42.5° C., 33% polyethylene glycol 1500, 47% polyethylene glycol 6000 and 20% distilled water, 49°–41° C.; 30% polyethylene glycol 1500, 40% polyethylene glycol 4000 and 30% polyethylene glycol 400, 33°–38° C.; mixtures of mono-, di-, and triglycerides of saturated fatty acids having 11 to 17 carbon atoms, 33°–35° C.; block polymer of 1,2-butylene oxide and ethylene oxide., block polymer of propylene oxide and ethylene oxide; block polymer of polyoxyalkylene and propylene glycol; petroleum based food grade waxes; and the like. The thermo-responsive composition is a means for storing a beneficial agent in a solid composition at a temperature of 25° C., maintaining an immiscible boundary at the swelling composition interface, and for dispensing the agent in a flowable composition at a temperature greater than 25° C., and preferably in the range of 25°–45° C. The thermo-responsive composition on being dispensed into a biological environment are easily excreted, metabolized, assimilated, or the like, for effective use of the beneficial agent.

Materials useful for forming internal wall 24 are materials used for forming a capsule. Capsule wall member 24 generally comprises a single piece or two piece construction, and in a presently preferred embodiment it is tubular shaped and it has a mouth at one end, and at the end distant therefrom it is closed in a hemispherical or dome shaped end. The capsule member serves as a hollow body having a wall that surrounds and defines an interior compartment provided with an opening for establishing communication with the exterior of the capsule and for filling the capsule. In one embodiment a capsule is made by dipping a mandrel, such as a stainless-steel mandrel, into a bath containing a solution of a capsule wall forming material to coat the mandrel with the material. Then, the mandrel is withdrawn, cooled and dried in a current of air. The capsule is stripped from the mandrel and trimmed to yield a capsule with an internal lumen. Materials used for forming capsules are the commercially available materials including gelatin, gelatin having a viscosity of 15 to 30 millipoises and a bloom strength up to 150 grams; gelatin having a bloom value of 160 to 250; a composition comprising gelatin, glycerine water and titanium dioxide; a composition comprising gelatin, erythrosin, iron oxide and titanium dioxide; a composition comprising gelatin, glycerine, sorbitol, potassium sorbate and titanium dioxide; a composition comprising gelatin, acacia, glycerin and water; water soluble polymers that permit the transport of water therethrough and can be made into capsules; and the like.

The expression "beneficial agent" as used herein denotes any beneficial agent or compound that can be delivered by device 10 to produce a beneficial and useful result. The beneficial agent can be from insoluble to very soluble in heat sensitive carrier means 16. The term, "beneficial agent" includes biocide, fungicide, larvicide, parasiticide, flukicides, medicine or drug, nutrient, vitamin, food supplement, mineral, anthelmintic, growth promotants and other agents that benefit the environment of use.

In the specification and the accompanying claims, the term "beneficial agent" includes any physiologically or pharmacologically active substances that produces a local or systemic effect in animals, including warm-blooded mammals, humans and primates, household, sport, farm and zoo animals. The term "physiologically" as used herein denotes the administration of a drug to produce normal levels and functions. The term "pharmacologically" denotes variations in response to an amount of drug administered to the host. *Stedman's Medical Dictionary*, 1966, published by Williams and Wilkins, Baltimore, Maryland. The beneficially active drugs that can be delivered by device 10 include inorganic and organic drugs, such as drugs that act on the central nervous system, depressants, hypnotics, sedatives, psychic energizers, tranquilizers, anticonvulsants, muscle relaxants, antiparkinson agents, analgesics, antiinflammatory, anesthetics, muscle contractants, antimicrobials, antimalarials, hormonal agents, contraceptives, diuretics, sympathomimetics, antiparasitics, neoplastics, hypoglycemics, opthalmics, electrolytes, cardiovascular drugs and the like.

Exemplary drugs that can be delivered by the delivery device prochlorperazine edisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridehexethyl chloride, phenformin hydrochloride, methylphenidate hydrochloride, oxprenolol hydrochloride, metroprolol tartrate, cimetidine hydrochloride, diphenidol, meclizine hydrochloride, prochlorperazine maleate, phenoxybenzamine, thiethylperazine maleate, anisindone, diphenadione, erythrityl tetranitrate, dizoxin, isofurophate, reserpine, acetazolamide, methazolamide, bendroflumethiazide, chloropropamide, tolazamide, chlormadinone acetate, phenaglycodol, allopurinol, aluminum aspirin, methotrexate, acetyl sulfisoxazole, erythromycin, progestins, esterogenic steroids, progestational steriods, corticosteroids, hydrocortisone, 17 $\beta$estradiol, ethenyl estradiol, ethinyl estradiol 3-methyl ester, presnisolong, hydrocorticosterone acetate, triamcinolone, methyltesterone, 17 $\beta$hydroxyprogesterone acetate, 19-nor-progesterone, norgestrel, norethindone, norethiderone, progesterone, norgesterone, norethynodrel, and the like.

Examples of other beneficial drugs that can be delivered by the delivery device include aspirin, indomethacin, naproxen, fenoprofen, sulindac, diclofenac, indoprofen, nitroglycerin, propranolol, valproate, timolol, atenolol, alprenolol, cimetidine, clonidine, imipramine, levodopa, chloropromazine, reserpine, methyl-dopa, dihydroxyphenylalanine, prvaloxyloxyethyl ester of $\alpha$-methyldopa hydrochloride, theophylline, calcium gluconate, ferrous lactate, vincamine, diazepam, phenoxybenzamine, blocking agents, and the like. The beneficial drugs are known to the art in *Pharmaceutical Sciences*, by Remington, 14th Ed., 1979, published by Mack Publishing Co., Easton, Pa.; *The Drug, The Nurse, The Patient, Including Current Drug Handbook*, 1974–1976, by Falconer et al., published by Saunder Co., Philadelphia, Pa., and *Medical Chemistry*, 3rd Ed., Vol. 1 & 2, by Burger, published by Wiley-Interscience, New York.

Representative of beneficial medicaments that can be delivered to warm-blooded animals, exemplified by ruminants using the delivery system of this invention, include anthelmintics such as mebendazole, levamisole, albendazole, cambendazole, fenbendazole, parbendazole, oxfendazole, oxybendazole, thiabendazole, tichlorfon, praziquantel, morantel and pirantel, and the like; antiparasitic agents such as avermectins and ivermectin, as disclosed in U.S. Pat. Nos. 4,199,569 and 4,389,397, both assigned to Merck & Co., and in *Science*, Vol. 221, pp 823-828, 1983, wherein said ivermectin antiparasitic drug are disclosed as useful for aiding in controlling commonly occurring infestations in animals, such as roundworms, lung worms and the like, and said ivermectin also being useful for the management of insect infestations such as grub, lice, mange mite, and the like; avermectin and milbemycin, antimicrobial agents such as chlortetracycline, oxytetracycline, tetracycline, gentamicin, streptomycin, dihydrostreptomycin, bacitracins, erthromycin, ampicillins, penicillins, cephalosporins, and the like; sulfa drugs such as sulfamethazine, sulfathiazole, and the like; growth-stimulants such as Monesin® sodium and Elfazepam®; defleaing agents such as dexamethazone and flumethazone; rumen fermentation manipulators and ionophores such as lasalocid, virginamycin, salinomycin and ronnel; minerals such as copper oxide, cobalt sulphate, sodium selenite, selenium, potassium iodate, zinc oxide, manganese sulphate, zinc sulphate and other mineral salts; anti-bloat agents such as organopoly siloxanes; hormone growth supplements such as stilbestrol; vitamines such as vitamin A, D and E; antienteritis agents such as furazolidone; growth efficiency factors such as β-agonists, elenbuterol; nutritional supplements such as lysine monohydrochloride, methionine, magnesium carbonate, and the like; and chemical markers such as chromic oxide, and salts of ytterbium and erbium..

The drug or agent can be in various forms, such as uncharged molecules, molecular complexes, pharmacologically acceptable salts such as hydrochlorides, hydrobromide, sulfate, laurylate, palmitate, phosphate, nitrate, borate, acetate, maleate, tartrate, oleate, salicylate, and the like. For acid drugs, salts of metals, amines, or organic cations, for example guaternary ammonium can be used. Derivatives of drugs such as esters, ethers, amides and the like can be used. Also, a drug or agent that is lipid insoluble can be used neat or in a form that is a lipid soluble derivative thereof, and on its release from the device can be converted by body activities to biologically active forms. Drugs that are water insoluble can be in form that is converted by enzymes, hydrolyzed by body pH or other metabolic processes to the original biologically active form. The amount of drug present in a device is initially in a present embodiment, an amount in excess of the amount that can be dissolved in the heat sensitive formulation. Generally, the device can contain from 0.05 ng to 10 g or more, with individual devices containing, for example, 25 ng, 1 mg, 5 mg, 125 mg, 250 mg, 500 mg, 750 mg, 1.5 g, 5 g, 10 g, and the like. The device of the invention can deliver from 0.1 mg/hr to 1500 mg/hr to the environment of use.

The wall, including the semipermeable, the microporous wall and the laminated wall can be formed by molding, air spraying, dipping or brushing with a wall forming composition. Other and presently preferred techniques that can be used for applying wall forming materials are the air suspension procedure and the pan coating procedures. The air procedure consists in suspending and tumbling the compartment forming materials in a current of air and a wall forming composition until the wall surrounds and coats the materials. The procedure can be repeated with a different wall forming composition to form a laminated wall. The air suspension procedure is described in U.S. Pat. No. 2,799,241; *J. Am. Pharm. Assoc.*, Vol. 48, pp 451-459, 1979; and ibid, Vol. 49, pp 82-84, 1960. Other standard manufacturing procedures are described in *Modern Plastics Encyclopedia*, Vol. 46, pp 62-70, 1969; and in *Pharmaceutical Sciences*, by Remington, 14th Ed., pp 1626-2678, 1970, published by Mack Publishing Co., Easton, Pa.

Exemplary solvents suitable for manufacturing the walls include inert inorganic and organic solvents that do not adversely harm the materials, the wall, the beneficial agent, the thermo-responsive composition, the expandable member, and the final dispenser. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, ethyl acetate, isopropyl acetate, n-gutyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naptha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Generally, for the present purpose the wall is applied at a temperature a few degrees less than the melting point of the thermo-responsive composition. Or, the thermoplastic composition can be loaded into the dispenser after applying the wall.

The expression "means for releasing a beneficial agent" as used herein includes at least one preformed passageway, or at least one passageway formed when the device is in use. The passageway, in either embodiment, will pass through the wall for communicating with the compartment for releasing the beneficial agent from the device. The expression "means for releasing a beneficial agent" modes passageway aperture, bore, pore, porous element through which the beneficial agent can migrate, hollow fiber, capillary tube, and the like. The means includes a material that is removed from the wall during use such as eroding in the environment of use to produce at least one passageway in the device. Representative materials suitable for forming a passageway include erodible poly(glycolic), poly(lactic) in the wall, gelatinous filaments, poly(vinyl alcohol), and the like. The passageway can be formed by leaching a material such as sorbitol from the wall. The passageway can have any shape such as round, triangular, square, elliptical, irregular, and the like. The device can be constructed with more than one passageway, especially for dispensing released agent over a wide area. In an embodiment, when the device is fabricated with more than one passageway they can be constructed as the functional equivalent of a single passageway. The passageway can be formed also by mechanical drilling or laser drilling through the wall. A description of means for releasing a beneficial agent as described herein is disclosed in U.S. Pat. Nos. 3,845,770 and 3,916,899. Procedures for forming at least one passageway of governed porosity by leaching from a cellulose wall a pore former is disclosed in U.S. Pat. Nos. 4,200,098; 4,235,236; 4,309,996, and 4,320,759. The leaching or dissolving of a pore former from a wall forming materials is known in U.S. Pat. Nos. 4,256,108; 4,265,874, and 4,344,929. Laser drilling equipment having photo detection means for orienting a device for selecting a surface for drilling a passageway for communicating with a preselected area inside a device are known in U.S. Pat. Nos. 4,063,064 and 4,088,864.

DESCRIPTION OF EXAMPLES OF THE INVENTION

The following examples are merely illustrative of the present invention and they should not be construed as limiting the scope of the invention in any way, as these examples and other equivalents thereof will become more apparent to those skilled in the art in the light of the present disclosure, the drawings and the accompanying claims.

EXAMPLE 1

A delivery device manufactured in the shape of an oral dispenser for administering to humans for the controlled delivery of indomethacin is made as follows: first, 300 mg of Butronic ®L-1 polyol, a block polymer formed by the polymerization of 1,2-butylene oxide to which ethylene oxide is added, as reported in *Cosmetics and Toiletries*, Vol. 97, pp 61–66, 1982, which polymer flow at a pour point of 39° C., is melted at 55° C. and then 200 mg of indomethacin is added thereto using a high sheer ultrasonic mixer. The resulting mixture is placed in a vacuum oven at 55° C. and the pressure reduced to less than 10 mm of mercury. The indomethacin-Butronic ® composition is allowed to remain in the vacuum for a period of about 10 minutes for removing entrapped air. Next, 400 mg of the resulting heat-sensitive thermoplastic drug formulation is poured into a 00 opened mouth gelatin capsule. Then, an expandable driving member comprising 100 mg of sodium chloride and 300 mg of the sodium salt of polyacrylic acid available as Carbopol ® 934P is compressed into a tablet. The tablet is formed using a 4 mm tableting tool and 3½ tons of compression force. The tablet has a final shape that corresponds to the internal shape of the opening of the capsule. The tablet member then is inserted into the opened end of the capsule until contact is made with the drug polyol formulation. Next, the capsule is coated in a pan coater with a rate controlling wall comprising 400 mg of 91% cellulose acetate butyrate and 9% polyethylene glycol 400. The wall is coated from a 5% wt/wt solution in methylene chloride methanol 90:10 v/v solvent system. The wall coated delivery systems then are dried at 30° C. for 24 hours. Next, a 30 mil exit passageway is drilled through the semipermeable wall using a high speed mechanical drill for communicating the drug formulation. The passageway establishes communication with the heat-responsive drug formulation for delivering it from the delivery system. Accompanying FIG. 6 depicts a laminate provided by the example comprising a first lamina means for absorbing thermal energy 16 containing agent 17 and a second lamina means for absorbing and/or imbibing fluid 18.

EXAMPLE 2

A delivery system is made according to the procedure set forth in Example 1, with the conditions as set forth, except that in this example, the heat-responsive composition comprises polyethylene glycol 400 distearate, and the expandable-swellable composition comprises 70% by weight of poly(ethylene oxide) having a molecular weight of 3,000,000 and 30% by weight of sodium chloride.

EXAMPLE 3

A dispenser system is prepared as follows: first, the body section of a capsule is positioned with its opened mouth in an upright position, and then a layer of an expandable-swellable composition is charged into the hemispherical end of the capsule. The composition comprises 25% by weight of osmotic solute sodium chloride, and 75% by weight of poly(ethylene oxide) having a molecular weight of 200,000. The expandable forming ingredients are blended in a commercial blender with heat for 20 minutes to yield a homogeneous composition. The heated composition is charged into the capsule forming a layer that occupies about ⅓ of the capsule. Next, a heat-sensitive drug formulation comprising an eutetic mixture of 77% neutral fat having a melting point of 35°–37° C. and 19.5% paraffin having a melting point of 52° C. is heated and 2.5% 2-acetoxybenzoic acid is added thereto. Then, the heated mixture is cooled to about 40° C. and injected into the capsule in contacting relation with the expandable layer, and the capsule allowed to cool to room temperature of 25° C.

Figure 7:
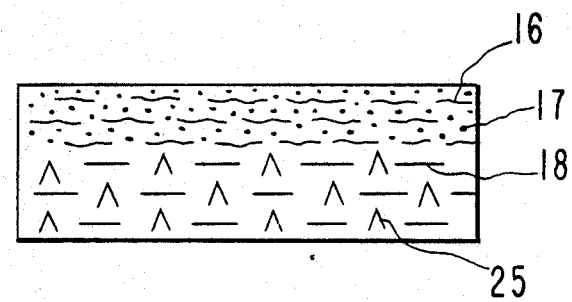

Then a solution of cellulose acetate, 15 weight percent, with an acetyl content of 39.8%, is prepared in a methylene chloride methanol solvent system and the capsule coated with a semipermeable wall. The wall is applied by dipping it into the coating solution for 15 times, first for a 5 second dip, then for two 10 second dips, then for a 30 second dip and then for 1 minute per dip, with an intervening 5 minute drying period. Following the dipping the delivery dispenser is dried at room temperature, 72° F. (about 22° C.) for 5 days in a current of dry air. The procedure applies about a 2 mm thick semipermeable wall. A passageway is laser drilled through the semipermeable wall connecting the exterior of the dispenser with the heat sensitive drug formulation for releasing it at a controlled rate over time. Accompanying FIG. 7 illustrates a laminate provided by the invention comprising a first lamina comprising means for absorbing thermal energy 16 and for containing a beneficial drug 17, and a second lamina in laminar arrangement comprising osmopolymer means for expanding 18 and for containing an osmagent 25, which exhibit a combined action of absorbing and/or imbibing fluid, expanding and occupying space in the compartment.

EXAMPLE 4

A dispensing device for delivering a beneficial agent to a warm-blooded animal is prepared as follows: first, a mold is filled with an expandable forming composition comprising 30 parts of ethyleneglycol monomethacrylate containing 0.12 parts of ethyleneglycol dimethacrylate and 10 parts of a 0.13% aqueous solution of sodium disulfate in aqueous ethanol. The composition polymerizes at 30° C., and after 20 minutes following equilibrium to room temperature, the solid layer is removed from the mold. Next, a layer of a heat-sensitive carrier comprising cocoa butter plus 2% beeswax and 250 mg of oxprenolol hydrochloride is placed in contact arrangement with the expandable composition. Then, the laminated arrangement is coated by quickly dipping with a microporous wall consisting essentially 45% by weight of cellulose acetate having an acetyl content of 39.8%, 45% by weight of sorbitol and 10% by weight of polyethylene glycol 400. Then, a semipermeable wall is coated onto a part of the microporous wall, except for an uncoated drug releasing surface. The semipermeable wall comprises 50% by weight of cellulose acetate having an acetyl content of 39.8% and 50% by weight of cellulose acetate having an acetyl content of 32%.

EXAMPLE 5

Figure 8:
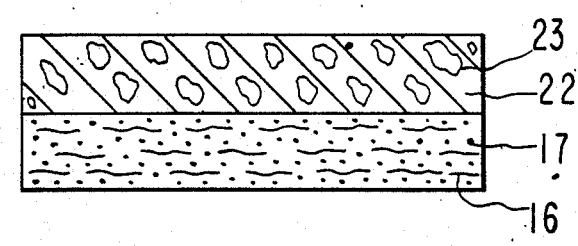
Figure 9:
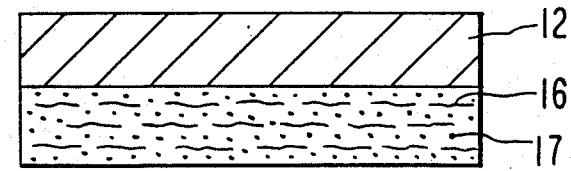

A delivery system is made according to the procedure set forth in Example 4, with the conditions and materials as set forth, except that in this example the device comprises a single wall of a varying thickness of cellulose acetate butyrate and polyethylene glycol 400. The thickness of the rate controlling wall varied from 30 mil (0.76 mm) at the end of device 10 to a uniform taper of 15 mil (0.38 mm) next to the passageway. Accompanying FIG. 8 illustrates a laminate provided by the invention comprising a microporous 22 composition containing pore former 23 in contact with a heat sensitive composition 16, and accompanying FIG. 9 illustrates a laminate comprising a semipermeable 12 composition contacting a heat sensitive composition 16, containing agent 17.

EXAMPLE 6

An osmotically activated dispensing system containing a thermoplastic drug formulation is manufactured as follows: first, 270 g of the neutralized sodium salt of Carbopol ®934P carboxypolymethylene, a carboxyvinyl polymer described in Chem. & Eng. News, Vol. 36, p 64, 1958, is combined with 116 g of dry sodium chloride and 4 g of magnesium stearate in a high speed blender. The resulting mixture is compressed on a Manesty D3B tablet press using a ¼ inch flat tooling die and 2 tons of pressure to yield 200 mg core-shaped tablets. Next, the resulting tablets are partially inserted into the larger half of a number 1 gelatin capsule having the dimensions of 258 mils outside diameter, 250 mils inside diameter, and 657 mils in length.

Then, a rate controlling membrane is prepared by dissolving 135 g of cellulose acetate butyrate and 15 g of polyethylene glycol, having an average molecular weight of 400, in 2,400 ml of methylene dichloride and methanol. The rate controlling wall is applied to the subassembly using a Freund HI-pan coater to yield an 8 mil thick membrane. After drying in a 50° C. over for forty minutes an orifice is formed in the wall by drilling and the drug reservoir is filled with an active formulation. The thermoplastic formulation is made by mixing 5.51 g of polyethylene glycol 400, 1.04 g of ivermectin and 0.35 g of Cubosic ® colloidal silicon dioxide in a vessel heated to 120° F. The reservoir is charged with 300 mg of the thermoplastic composition. The resulting device releases ivermectin at a rate of 0.2 mg/hr for approximately 72 hours.

EXAMPLES 7-11

The procedure of Example 6 is repeated with the conditions as described except for the driving hydrogel which, in these examples, comprises 100% sodium carboxyvinyl polymer; 100% poly(oxyethylene) coagulant; 85:15 sodium carboxyvinyl polymer:sodium chloride; 85:15 poly(oxyethylene) coagulant:sodium chloride; and, 70:30 poly(oxyethylene) coagulant:sodium chloride.

EXAMPLE 12

The procedure of Example 6 is repeated with all conditions as previously set forth except that in this example the semipermeable wall is a laminate comprising an inner lamina of cellulose acetate having an acetyl content of 32% coated with an outer lamina comprising cellulose acetate having an acetyl content of 39.8%

EXAMPLE 13

The procedure of Example 6 is repeated with all conditions as set forth, except that in this example the thermoplastic composition comprises 20.1 g L-1 polyol, a block polymer formed by the polymerization of 1,2-butylene oxide to which ethylene oxide is added, as reported in Cosmetics and Toiletries, Vol. 97, pp 61–66, 1982; 2.44 g of ivermectin and (a) 70:30 sodium Carbopol ®934P:sodium chloride;.(b) 85:15 poly(oxyethylene) coagulant:sodium chloride, and (c) 100% poly(oxyethylene oxide).

EXAMPLE 14

The procedure of Example 6 is repeated with all conditions as described, except that in this example 105 g of polyethylene glycol distearate 400 is mixed with 9.9 g of ivermectin and the Cabosil ® is omitted from the formulation.

An embodiment of the invention pertains to a method of increasing the deliverability of a beneficial agent by formulating a heat-sensitive composition containing a beneficial agent and, another embodiment of the invention pertains to making the delivery system of the invention. An embodiment of the invention pertains also to a method for administering a beneficial drug at a controlled rate to an animal which method comprises the steps of: (a) admitting orally into the animal a dispensing device comprising: (1) an outer wall means comprising in at least a part of a semipermeable polymeric composition permeable to the passage of fluid and substantially impermeable to the passage of drug, the wall surrounding: (2) an internal lumen containing a layer of a beneficial drug formulation comprising a dosage unit amount of drug for preforming a therapeutic program in a heat-sensitive pharmaceutically acceptable means that melts at body temperature and is a carrier means for transporting the drug from the dispenser; (3) a layer of an expandable means in the lumen; and, (4) at least one dispensing means in the wall communicating with the heat-sensitive drug formulation; (b) imbibing fluid through the wall at a rate determined by the permeability of the wall and the osmotic pressure gradient across the wall causing the layer of expandable hydrogel to expand and swell; (c) melting the drug formulation to form a flowable formulation; and, (d) delivering the beneficial drug formulation from the compartment by the expandable layer continually expanding against the melting formulation causing the formulation to be dispensed in a therapeutically effective amount through the dispensing means at a controlled rate to the animal over a prolonged period of time.

It will be readily appreciated the present invention contributes to the dispensing art an unobvious delivery device having wide and practical application. The invention comprising a heat-sensitive means and an expandable means operating together for dispensing a beneficial agent at a controlled rate. It is unobvious, as it is unexpected that a pair of means could physically change with one means forming a dispensable composition that is urged simultaneously by an expanding means from the device over time. In as much as the foregoing specification comprises preferred embodiments of the invention, it is understood that variations and modifications may be made herein in accordance with the inventive principles disclosed, without departing from the scope of the invention.

We claim:

1. A delivery device for delivering a beneficial agent formulation to an environment of use, the delivery device comprising;
   (a) wall means that surrounds and defines an internal compartment;
   (b) means in the compartment for expanding and occupying an increasing area of the compartment;
   (c) means in the compartment for absorbing thermal energy from the environment and for carrying a beneficial agent;
   (d) a dosage unit amount of a beneficial agent present in the means for absorbing thermal energy from the environment; and,
   (e) means in the wall for delivering the beneficial agent from the delivery device to the environment over time.

2. The delivery device for delivering the beneficial agent formulation to the environment according to claim 1, wherein the wall means that surrounds and defines the compartment comprises at least in part a semipermeable composition.

3. The delivery device for delivering the beneficial agent formulation to the environment according to claim 1, wherein the wall means that surrounds and defines the compartment comprises a first polymeric composition that permits the passage of fluid present in the environment of use and is substantially impervious to the passage of a beneficial agent and a second polymeric composition that permits the passage of an external fluid and the passage of a beneficial agent.

4. The delivery device for delivering the beneficial agent formulation to the environment according to claim 1, wherein the means in the wall for delivering the beneficial agent comprises at least one passageway.

5. the delivery device for delivering the beneficial agent formulation to the environment according to claim 1, wherein the means in the wall for delivering the beneficial agent comprises at least one passageway formed when the delivery device is in use.

6. The delivery device for delivering the beneficial agent formulation to the environment of use according to claim 1, wherein the means in the wall for delivering the beneficial agent from the device comprises a passageway forming material that is removed from the means when the device is in operation in the environment of use.

7. The delivery device for delivering the beneficial agent formulation to the environment according to claim 1, wherein the means in the wall for delivering the beneficial agent is a passageway.

8. The delivery device for delivering the beneficial agent formulation to the environment according to claim 1, wherein the wall means that surrounds and defines the compartment comprises at least in part a microporous member.

9. The delivery device for delivering the beneficial agent formulation to the environment according to claim 1, wherein the wall means that surrounds and defines the compartment comprises a microporous member laminated in part by a semipermeable member.

10. The delivery device for delivering the beneficial agent formulation to the environment of use according to claim 1, wherein the means for absorbing thermal energy forms a dispensable composition at a temperature of 25° C. to 45° C. in an environment having a temperature of 25° C. to 45° C.

11. The delivery device for delivering the beneficial agent formulation to the environment of use according to claim 1, wherein the wall means comprises a member selected from the group consisting of a cellulose ester, cellulose diester, cellulose triester, cellulose ether, cellulose ester-ether, cellulose acylate, cellulose diacylate, and cellulose triacylate.

12. The delivery device for delivering the beneficial agent formulation to the environment of use according to claim 1, wherein the wall means comprises a member selected from the group consisting of a cellulose ester, cellulose diester, cellulose triester, cellulose ether, cellulose ester-ether, cellulose acylate, cellulose diacylate, cellulose triacylate, and a pore former.

13. The delivery device for delivering the beneficial agent formulation to the environment of use according to claim 1, wherein the means for expanding and occupying an increasing area comprises the sodium salt of polyacrylic acid and sodium chloride.

14. The delivery device for delivering the beneficial agent formulation to the environment of use according to claim 1, wherein the means for expanding and occupying an increasing area is a member selected from the group consisting essentially of poly(ethylene oxide), poly(acrylamide), poly(hydroxyalkyl acrylate), poly(acrylic acid), and poly(saccharide).

15. The delivery device for delivering the beneficial agent formulation to the environment of use according to claim 1, wherein the wall means comprises at least in part a member selected from the group consisting of an olefin polymer, a vinyl polymer, a condensation polymer, a rubber polymer, a silicon polymer and a carbohydrate polymer.

16. The delivery device for delivering the beneficial agent formulation to the environment of use according to claim 1, wherein the wall comprises a member selected from the group consisting of cellulose acetate, cellulose acetate butyrate and cellulose propionate morpholinobutrate.

17. The delivery device for delivering the beneficial agent formulation to the environment of use according to claim 1, wherein the wall comprises a member selected from the group consisting of cellulose acetate butyrate, cellulose acetate morpholinobutrate and cellulose acetate phthalate, and a pore former blended with the member.

18. A laminate useful for manufacturing a delivery device for delivering a beneficial agent to a warm-blooded animal, wherein the laminate comprises lamina means for housing a beneficial agent and for absorbing heat from the animal for forming a deliverable composition, and lamina means for absorbing fluid from the animal for increasing in volume and urging the deliverable composition from a delivery device.

19. A laminate useful for manufacturing a delivery device for delivering a beneficial agent to a warm-blooded animal, wherein the laminate comprises a microporous lamina means for releasing a beneficial agent formulation from a dispensing device, and a lamina means for containing a beneficial agent and for absorbing heat from the animal for forming a dispensable composition that is delivered through the microporous lamina from the dispensing device.

20. A laminate useful for manufacturing a delivery device for delivering a beneficial agent to an environment of use, said laminate comprising semipermeable lamina means for admitting a fluid into the delivery device, and lamina means for absorbing heat and softening at a temperature of at least 25° C.

21. A delivery system for delivering a beneficial agent formulation to an environment of use, the delivery system comprising:
    (a) a hollow body member having an internal lumen;
    (b) a heat sensitive formulation in the lumen that forms a deliverable formulation at a temperature of at least 25° C.;
    (c) a beneficial agent present in the heat sensitive formulation;
    (d) means in the lumen for expanding from a first size to an increased size, said means adjacent to the heat sensitive formulation;
    (e) a wall surrounding the hollow body, the wall formed in at least a part of a composition that is permeable to the passage of fluid; and,
    (f) at least one passageway in the wall communicating with the heat sensitive formulation for delivering the formulation to the environment of use at a controlled rate over a prolonged period of time.

22. A composition comprising a first means for manufacturing a dispensing device and a second means for manufacturing a dispensing device, which dispensing device comprises an internal lumen for housing the first and second means, and wherein said first means comprises a thermo-responsive composition that melts as a temperature of from 25° C. to 45° C., is a carrier for a beneficial agent and contains a beneficial agent that produces a beneficial effect when administered to an animal, and wherein said second means comprises a polymeric composition that expands and swells in the presence of an aqueous fluid.

23. A delivery device for delivering a beneficial agent formulation to an environment of use, the delivery device comprising:
    (a) wall means that surrounds and defines an internal compartment;
    (b) means in the compartment for attracting an external aqueous fluid into the compartment for forming an area comprising, in combination, the means and the external aqueous fluid, which combination occupies an increasing area in the compartment as beneficial agent is delivered from the delivery device;
    (c) means in the compartment for absorbing thermal energy from the environment of use and for transporting a beneficial agent;
    (d) a dosage unit amount of a beneficial agent for delivery to the environment of use in the compartment; and,
    (e) means in the wall for delivering the beneficial agent from the delivery device to the environment of use over time.

* * * * *